United States Patent
Johnson et al.

(10) Patent No.: US 10,261,277 B2
(45) Date of Patent: Apr. 16, 2019

(54) SHEATHED OPTICAL FIBER

(71) Applicant: UVL Blood Labs, Inc., Santa Barbara, CA (US)

(72) Inventors: Scot Johnson, Lutz, FL (US); Michael Harter, Tampa, FL (US)

(73) Assignee: UVLrx Therapeutics, Inc., Oldsmar, FL (US)

( * ) Notice: Subject to any disclaimer, the term of this patent is extended or adjusted under 35 U.S.C. 154(b) by 833 days.

(21) Appl. No.: 14/323,180

(22) Filed: Jul. 3, 2014

(65) Prior Publication Data

US 2015/0011837 A1    Jan. 8, 2015

Related U.S. Application Data

(60) Provisional application No. 61/957,464, filed on Jul. 3, 2013, provisional application No. 61/957,465, filed on Jul. 3, 2013, provisional application No. 61/887,670, filed on Oct. 7, 2013.

(51) Int. Cl.
| | |
|---|---|
| *A61B 1/06* | (2006.01) |
| *G02B 6/44* | (2006.01) |
| *A61B 18/24* | (2006.01) |
| *A61N 5/06* | (2006.01) |
| *F21V 8/00* | (2006.01) |
| *G02B 6/26* | (2006.01) |

(52) U.S. Cl.
CPC .............. *G02B 6/443* (2013.01); *A61B 18/24* (2013.01); *G02B 6/0008* (2013.01); *A61N 5/0601* (2013.01); *A61N 2005/063* (2013.01); *G02B 6/0006* (2013.01); *G02B 6/262* (2013.01)

(58) Field of Classification Search
None
See application file for complete search history.

(56) References Cited

U.S. PATENT DOCUMENTS

| | | | |
|---|---|---|---|
| 4,693,556 A | 9/1987 | McCaughan, Jr. | |
| 4,718,417 A * | 1/1988 | Kittrell ............. | A61B 1/00183 600/317 |
| 5,242,437 A | 9/1993 | Everett et al. | |
| 5,310,964 A | 5/1994 | Roberts et al. | |
| 5,349,590 A | 9/1994 | Amirkhanian et al. | |
| 5,505,725 A | 4/1996 | Samson | |
| 5,637,877 A | 6/1997 | Sinofsky | |
| 6,312,593 B1 | 11/2001 | Petrie | |

(Continued)

FOREIGN PATENT DOCUMENTS

| | | |
|---|---|---|
| EP | 0951305 B1 | 10/2004 |
| EP | 2179767 A1 | 4/2010 |
| WO | 2006128047 A2 | 11/2006 |

*Primary Examiner* — Sameh Boles
(74) *Attorney, Agent, or Firm* — The Emanuelson Firm; Kenneth T. Emanuelson

(57) ABSTRACT

An optical device for illuminating the vasculature of a mammal using ultraviolet, visible, and/or infrared light is described. The optical device includes an optical fiber encased in a biocompatible sheath, and is dimensioned to lie within an intravascular catheter. When placed within a vascular space and coupled with a suitable light source the optical device illuminates the vascular space and its contents. The faces of the optical fiber are configured to optimize the capture of ultraviolet, visible, and/or infrared light from a light source without the use of active optics.

14 Claims, 2 Drawing Sheets

(56) References Cited

U.S. PATENT DOCUMENTS

| | | |
|---|---|---|
| 6,908,460 B2 | 6/2005 | DiStefano |
| 8,460,229 B2 | 6/2013 | Dacey, Jr. et al. |
| 2003/0127603 A1 | 7/2003 | Horowitz et al. |
| 2004/0073278 A1 | 4/2004 | Pachys |
| 2004/0186407 A1 | 9/2004 | Walker et al. |
| 2013/0101464 A1 | 4/2013 | Smyczynski |
| 2014/0051966 A1 | 2/2014 | Irisawa |

* cited by examiner

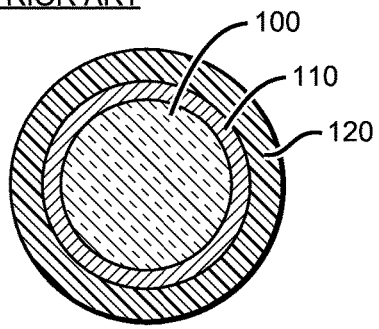
FIG. 1A
PRIOR ART
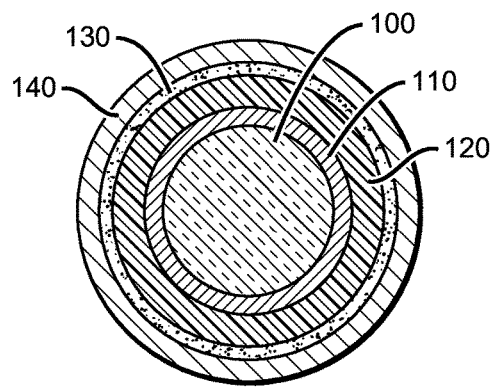
FIG. 1B
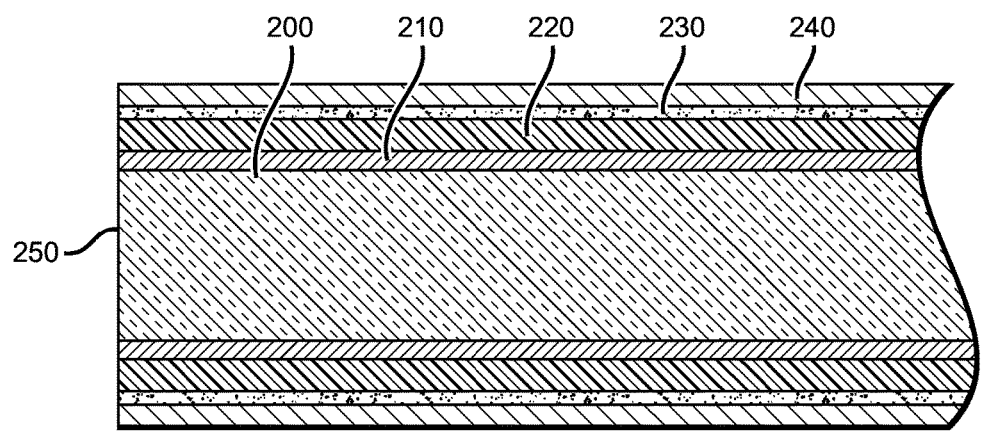
FIG. 2
FIG. 3
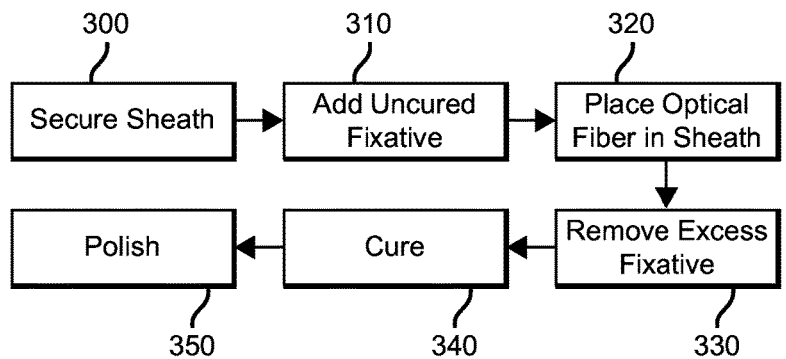

| 18 gauge catheter | in | mm |
|---|---|---|
| Catheter ID | 0.0360 | 0.9144 |
| Catheter ID area | 0.0010 | 0.0259 |
| ID of a 24 gauge catheter (desired flow rate) | 0.0120 | 0.3048 |
| Sectional area of a 24 gauge catheter | 0.0001 | 0.0029 |
| Residual sectional area remaining | 0.0009 | 0.0230 |
| Calculated maximum allowable sheath radius | 0.0170 | 0.4311 |
| Calculated maximum allowable sheath diameter | 0.0339 | 0.8621 |
| 21 gauge XTW type tube: OD | 0.0320 | 0.8128 |
| 21 gauge XTW type tube: ID | 0.0250 | 0.6350 |
| Optical fiber with effective OD of 600μm | 0.0236 | 0.6000 |
| Gap diameter | 0.0014 | 0.0350 |
| Gap spacing | 0.0007 | 0.0175 |

| 20 gauge catheter | in | mm |
|---|---|---|
| Catheter ID | 0.0280 | 0.7112 |
| Catheter ID area | 0.0006 | 0.0156 |
| ID of a 24 gauge catheter (desired flow rate) | 0.0120 | 0.3048 |
| Sectional area of a 24 gauge catheter | 0.0001 | 0.0029 |
| Residual sectional area remaining | 0.0005 | 0.0128 |
| Calculated maximum allowable sheath radius | 0.0126 | 0.3213 |
| Calculated maximum allowable sheath diameter | 0.0253 | 0.6426 |
| 23 gauge XTW type tube: OD | 0.0250 | 0.6350 |
| 23 gauge XTW type tube: ID | 0.0190 | 0.4826 |
| Optical fiber with effective OD of 480μm | 0.0189 | 0.4800 |
| Gap diameter | 0.0001 | 0.0026 |
| Gap spacing | 0.0001 | 0.0013 |

| 22 gauge catheter | in | mm |
|---|---|---|
| Catheter ID | 0.0220 | 0.5588 |
| Catheter ID area | 0.0004 | 0.0097 |
| ID of a 24 gauge catheter (desired flow rate) | 0.0120 | 0.3048 |
| Sectional area of a 24 gauge catheter | 0.0001 | 0.0029 |
| Residual sectional area remaining | 0.0003 | 0.0068 |
| Calculated maximum allowable sheath radius | 0.0092 | 0.2342 |
| Calculated maximum allowable sheath diameter | 0.0184 | 0.4684 |
| 26 gauge XTW type tube: OD | 0.0280 | 0.7112 |
| 26 gauge XTW type tube: ID | 0.0140 | 0.3556 |
| Optical fiber with effective OD of 330μm | 0.0130 | 0.3300 |
| Optical fiber with effective OD of 240μm | 0.0094 | 0.2400 |
| Gap diameter (330μm) | 0.0010 | 0.0256 |
| Gap space (330 μm) | 0.0005 | 0.0128 |
| Gap diameter (240μm) | 0.0046 | 0.1156 |
| Gap space (240μm) | 0.0023 | 0.0578 |

FIG. 4

SHEATHED OPTICAL FIBER

This application claims priority to U.S. Provisional Application No. 61/957,464 filed on Jul. 3, 2013, U.S. Provisional Application No. 61/957,465 filed on Jul. 3, 2013, and U.S. Provisional Application No. 61/887,670 filed on Oct. 7, 2013. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

This application is related to co-pending U.S. patent application Ser. No. 14/323,217, now U.S. Pat. No. 9,827,438, titled "Vascular Access Device with Integrated Light Guide", co-pending international patent application Ser. No. PCT/US2014/045460, titled "Vascular Access Device with Integrated Light Guide", co-pending U.S. patent application Ser. No. 14/323,244, now U.S. Pat. No. 9,814,899, titled "Systems and Methods for In Vivo Irradiation of Blood", and co-pending international patent application Ser. No. PCT/US2014/045465, titled "Systems and Methods for In Vivo Irradiation of Blood". All of these co-pending U.S. and international patent applications are incorporated by reference herein in their entirety.

FIELD OF THE INVENTION

The present invention generally relates to devices and methods for treatment of human blood. More particularly, the present invention relates to devices and methods for irradiating human blood in vivo.

BACKGROUND

It has long been accepted that certain wavelengths of electromagnetic radiation, such as ultraviolet light, have the ability to affect biological and chemical structures. For example, the formation of thymine dimers under the influence of ultraviolet light is well known and has been utilized to sterilize surfaces by killing or inactivating a variety of pathogens. In the early 1900's efforts were made to incorporate exposure to ultraviolet light as a treatment modality for various diseases, including bacterial and viral infections. Procedures were typically extracorporeal; a volume of blood would be removed from a patient, irradiated to modify a patient's immune response and/or inactivate pathogens, and returned to the patient. Such efforts were hindered, however, by the sources of ultraviolet light available at the time. UV lamps of the time period did not operate reliably, produced inconsistent illumination, and generated large amounts of heat. The development of effective and reliable antibiotics that were easily administered resulted in a loss of interest in this therapeutic approach.

The increasing prevalence of antibiotic-resistant pathogens and the recognition of potential effectiveness for the treatment of noninfectious medical conditions has led to an increasing interest in the use of blood irradiation as a treatment modality. A variety of devices for improved extracorporeal irradiation of blood have been proposed. For example, International Patent Application No. WO2006128047 (to W. F. Harding et al) and United States Patent Application No. 2006/157,426 (to T. R. Petrie) disclose devices for the irradiation of volumes of blood taken from a patient using devices that incorporate shutters or similar mechanisms that allow finer control of the degree of irradiation. Other extracorporeal devices have included mechanisms for mixing the volume of blood taken from the patient in order to improve exposure during the irradiation process. Both active agitation of blood (European Patent No. EP0951305B1, to L. B. Morris) and use of static mixers with plasma preparations (United States Patent Application No. 2003/127,603, to B. Horowits, X. Wang, and L. D. Barr) have been disclosed. Approaches involving the removal and reinfusion of a specific volume of blood are, however, necessarily limited in their ability to irradiate large blood volumes from an individual. In addition, they expose the patient to the risk of reinfusion with treated blood from a different individual, through either mislabeling or human error. Approaches in which blood is removed, irradiated, and returned to the patient in a continuous fashion have been described (United States Patent Application No. 2013/0,101,464 to M. S. Smyczynski), however such extracorporeal approaches necessarily involve the use of complex equipment, damage to blood cells and platelets through exposure to equipment surfaces, and formation of blood clots.

Alternative methods for the irradiation of blood have been proposed. For example, European Patent Application No. 2,179,767 A1, to F. Kokos and L. Jurinyi, discloses a device for irradiation of blood through the membranes of the patient's nasal mucosa. Various devices have also been developed that permit direct irradiation of blood or tissue within the vasculature or body cavity of a patient. For example, U.S. Pat. No. 4,693,556 (to McCaughan) describes placing an optical fiber equipped with an optical radiator into a body cavity. U.S. Pat. No. 5,505,725 (to Samson) describes instilling an optical fiber directly into a vein by insertion through a hypodermic needle. Such approaches, however, fail to provide for the accidental breakage of the inserted optical fiber and the subsequent loss of efficient irradiation and release of the resulting fragments into circulation. Such breakage is a known issue with quartz or silica materials that are typically utilized in optical fibers transmitting, particularly when subjected to relatively sharp bends such as upon insertion into a vein. In addition, such optical fibers lack sufficient rigidity to remain in one position within a vein when subjected to the pulsatile flow of blood, and may collide with and damage the interior of the vein. U.S. Pat. No. 5,053,033 (to Clarke) and U.S. Pat. No. 7,811,281 (to Rentrop) describe the use of plastic catheters with imbedded optical fiber for delivering light energy to the site of atherosclerotic plaques. These, however, lack features that prevent the fiber optic from bending to the point of fragmentation and may not be compatible with smaller peripheral blood vessels.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

While certain devices and methods are known in the art to irradiate blood, all or almost all of them suffer from one or more disadvantages. Thus, there is still a need for simple device for the effective in vivo irradiation of blood.

SUMMARY OF THE INVENTION

The inventive subject matter provides a sheathed optical fiber useful in illuminating the vasculature of a vertebrate and methods for manufacturing and using such a sheathed optical fiber. The sheathed optical fiber includes an optical fiber that lies within the lumen of a hollow sheath, with at least a portion of the space remaining within the lumen of the sheath occupied by a fixative. The sheath is dimensioned to facilitate placement within a vascular space, and the exposed faces of the optical fiber are machined and polished to provide efficient optical coupling without the need for active optics.

In one embodiment of the inventive concept, a sheathed optical fiber includes a sheath with a lumen and an optical fiber. The optical fiber includes a core, a cladding, and a jacket, and the core is composed of a material that is substantially transparent to ultraviolet, visible, and/or infrared wavelengths of light (for example, silica). The sheath is composed of a biologically compatible material, such as passivated stainless steel. The sheath can be pliant, permitting a degree of flexion, and can also be resilient. The entirety of the optical fiber lies within the lumen of the sheath and has the same length as the sheath, such that the ends of the optical fiber and the ends of the sheath coincide. The diameter of the optical fiber is less than the diameter of the sheath's lumen, and at least part (for example, at least 95%) of the volume within the sheath that is not occupied by the optical fiber is occupied by a fixative. The fixative is distributed throughout this volume so as to contain fragments of the optical fiber (should the optical fiber be damaged or broken), and can be transparent to ultraviolet and/or visible light. In some embodiments the fixative is resistant to degradation when exposed to pharmaceutically acceptable solutions, and can be an epoxy resin. The ends of the optical fiber are substantially perpendicular to the major axis of the sheathed optical fiber and are polished to a surface roughness of 0.3 microns or less. The diameter of the sheathed optical fiber permits it to lie within a lumen of an intravenous catheter, leaving an average distance of about 0.04 mm or more between the surface of the sheathed optical fiber and the wall of the lumen of the catheter, assuming a typical sheathed outer diameter of 0.75 mm or less.

Another embodiment of the inventive concept is a method of illuminating a vasculature using a sheathed optical fiber. In such an embodiment a sheathed optical fiber having a sheath, an optical fiber, and a fixative is placed within a vascular space, and electromagnetic energy is applied to the sheathed optical fiber. The optical fiber is the same length as the sheath and lies entirely within a lumen of the sheath, with a fixative occupying some or all of the space within the lumen that is not occupied by the optical fiber.

Still another embodiment of the inventive concept is a method for manufacturing a sheathed optical fiber. In this method a volume of uncured fixative is placed within the lumen of a sheath. An optical fiber having a core, cladding, and a jacket is then advanced through the lumen, beginning at the end of the sheath through which the uncured fixative was introduced. After the desired length of optical fiber has been placed in the lumen excess uncured fixative is removed, and the remaining fixative is cured. The exposed ends of the optical fiber are then polished to a roughness of 0.3 microns or less. In some embodiments the length of the optical fiber and the sheath are essentially identical.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1A depicts a cross section of a prior art optical fiber.
FIG. 1B depicts a cross section of a sheathed optical fiber of the inventive concept.

FIG. 2 depicts a longitudinal section of a sheathed optical fiber of the inventive concept.

FIG. 3 schematically depicts a flow chart of a method of manufacturing a sheathed optical fiber of the inventive concept.

FIG. 4 provides examples of calculations that can be used to determine acceptable optical device and optical fiber dimensions.

DETAILED DESCRIPTION

An optical appliance for the safe, efficient, and convenient illumination of the vasculature of a mammal is provided herein. Such illumination can, for example, be provided for the purposes of photodynamic therapy. Such photodynamic therapy can be provided to flowing blood that is proximal to the fiber optic appliance when it is in use, and the fiber optic appliance can be configured to optimize the delivery of electromagnetic energy towards that end. For example, a terminus of the fiber optic appliance is configured to optimize delivery of electromagnetic energy from a source of such energy to an optical fiber component without the use of bulky and difficult to align active optics (for example, a lens), which decreases the utility of such a device in a photodynamic therapy setting. Similarly, a terminus of the fiber optic appliance is configured to deliver electromagnetic energy at high intensity over a volume that is appropriate to provide adequate coverage of a segment of a peripheral blood vessel (such as a blood vessel that is conveniently located for safe and relatively painless application of photodynamic therapy). The fiber optic based appliance also includes a biocompatible sheath that provides a degree of stiffness and resilience to an optical fiber that aids proper placement, while containing fragments of such an optical fiber thereby preventing such fragments from entering the circulatory system should breakage occur.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

A cross section of an optical fiber of the prior art is shown in FIG. 1A. Such an optical fiber includes a core 100, a cladding 110, and a jacket 120. The core 100 is made from a light-transmitting plastic, quartz, silica, or similar transmissive material. The cladding 110 has a refractive index that differs from that of the core, and results in total internal reflectance of light through the core and efficient transfer of light through the optical fiber. The jacket 120 provides a degree of mechanical support for the core 100 and the cladding 110, and is typically made from polyimide.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. Similarly, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

A cross section of an optical device of the inventive concept is shown in FIG. 1B. An optical fiber suitable for use in embodiments of the inventive concept can be single-mode fiber or a multi-mode fiber. A core 100 of material that transmits electromagnetic radiation is provided. In a preferred embodiment the core 100 efficiently transmits both ultraviolet (i.e. UVA, UVB, and/or UVC) and visible wavelengths of light. Suitable optical fibers have an attenuation of less than 2 dB/m at wavelengths ranging from about 200 nm to about 400 nm, and less than 200 dB/km at wavelengths ranging from about 400 nm to about 900 nm. Suitable materials for the core 100 include silica, fluorozirconate, fluoroaluminate, chalcogenide glass, and/or sapphire. Polymers, such as polymethylmethacrylate, polystyrene, polycarbonate, and/or perfluorinated polymers (for example poly (perfluoro-butenylvinyl ether)) can also be used. In a preferred embodiment of the inventive concept the core 100 is at least partially composed of silica. This is counterintuitive, as silica is relatively fragile and would not generally be considered a suitable material for placement in the vasculature. The core 100 is surrounded by a cladding 110, for example a doped silica, that has an index of refraction that supports internal reflectance along the core of ultraviolet, visible, and/or infrared light and enables efficient transmission. The cladding 110 is surrounded by a jacket 120. Suitable materials for the jacket 120 include acrylate, silicone, polyimide, polyurethane, and/or polyvinylchloride. In a preferred embodiment of the inventive concept the jacket 120 is at least partially made of polyimide. In some embodiments the jacket 120 can be removed from the optical fiber prior to assembly of the sheathed optical fiber or, alternatively, an optical fiber can be used that was manufactured without a jacket 120.

In some embodiments of the inventive concept a terminus of the optical fiber can be modified to incorporate an active optical element, such as a lens or prism, that serves to redistribute light exiting the optical fiber. For example, a terminus of an optical fiber could be ground or otherwise sculpted such that the core 100 or the core 100 and cladding 110 provide a partially spherical (for example hemispherical) lens, a plano-concave lens, or a plano-convex lens. Alternatively, a terminus of an optical fiber could be ground or otherwise sculpted to a predetermined angle to form a prism. In another embodiment of the inventive concept, a lens, prism, or other device is affixed to a terminus of the optical fiber (for example, using heat, friction, and/or a suitable adhesive) to receive electromagnetic energy that exits the optical fiber. In such embodiments the lens or prism can serve to redirect, collimate, focus, and/or disperse electromagnetic energy as it exits the fiber optic component of the sheathed optical fiber, thereby providing a more desirable dispersion of the electromagnetic energy.

The outer diameter of the jacket 120 is selected to fit within a sheath 140 as described below. Suitable diameters for the jacket 120 range from about 60 µm to about 1400 µm. In other embodiments of the inventive concept the diameter of the jacket 120 ranges from about 450 µm to about 1300 µm. In a preferred embodiment of the inventive concept the diameter of the jacket 120, and hence the optical fiber, is 480 µm (±7 µm) or smaller.

The optical device of the inventive concept shown in FIG. 1B additionally includes a sheath 140. The sheath 140 is made of a biocompatible material, for example nylon, polycarbonate, fluoropolymers, titanium, titanium/aluminum alloys, stainless steels (for example, 304 stainless steel), and/or cobalt/chromium/molybdenum alloys. The material of the sheath 140 is selected to provide a degree of stiffness that permits accurate placement of the optical device within the vasculature, for example holding it in a suitable central location within a peripheral vein. The material of the sheath 140 is also selected to provide a degree of resilience, such that the optical device can be bent or angled slightly, for example during the process of insertion into the vasculature, and maintain an essentially straight or slightly curved configuration. In a preferred embodiment the sheath 140 is at least partially composed a passivated stainless steel.

In a preferred embodiment the sheath 140 can be constructed from hollow tubing, such as that utilized in the production of hypodermic needles used for access to the peripheral vasculature. The size of such tubing is frequently expressed as a gauge; tubing ranging from 27 gauge to 6 gauge is considered suitable for use as a sheath. This corresponds to an outer diameter ranging from about 0.4 mm to about 5.2 mm. In some embodiments tubing ranging from 23 gauge (an outer diameter of about 0.64 mm) to 16 gauge (an outer diameter of about 1.5 mm) is utilized as a sheath. In a preferred embodiment, 23 gauge tubing with an outer diameter of about 0.64 mm is used. In such embodiments the diameter of the jacket 120 is selected to be smaller than that of the internal diameter of the sheath 140. In some embodiments, 21 gauge tubing (with an outer diameter of about 0.81 mm and an inner diameter of about 0.64 mm) is used in conjunction with an optical fiber having an outer diameter of about 0.63 mm. In still another embodiment of the inventive concept, 26 gauge tubing (with an outer diameter of about 0.46 mm and an inner diameter of about 0.36 mm) is used in conjunction with an optical fiber having an outer diameter of about 0.35 mm. In a preferred embodiment, 23 gauge tubing with an outer diameter of about 0.64 mm and an inner diameter of about 0.485 mm is used in conjunction with an optical fiber having an outer diameter of about 0.482 mm. The use of optical fibers that lack a jacket 120 is contemplated, and it should be appreciated that such embodiments permit the use of optical fibers with cores 100 of larger diameter than when optical fibers with jackets are used. As a result, use of unjacketed optical fibers can provide more effective transmission of light.

Use of a jacket 120 with a diameter less than that of the internal diameter of the sheath 140 necessarily leaves a gap or intraluminal space 130 between the inner wall of the sheath 140 and the surface of the jacket 120. In some embodiments the average span of this gap 130 can range from 0.1 µm to 60 µm. In other embodiments the average span of this gap 130 can range from about 0.2 μm to about 20 μm. In a preferred embodiment the average width of this gap 130 is about 1.3 μm.

In an optical device of the inventive concept at least a portion of this gap 130 is occupied by a fixative. This fixative is distributed so as to effectively contain fragments of the core 100, cladding 110, and/or jacket 120 within the sheath 140 in the event of breakage. For example, the fixative can be distributed across essentially the entirety (i.e. greater than 95%) of the length of the gap 130. Alternatively, the fixative can be distributed such that it occupies at least portions of the gap 130 at or near the termini of the optical device. The fixative can occupy at least 50%, 60%, 70%, 80%, 90%, or more of the gap 130. In a preferred embodiment of the inventive concept the fixative fills essentially the entire (i.e. greater than 95%) volume of the gap 130.

Suitable fixatives are available as flowable or liquid precursors that cure (i.e. react, set, cool, or otherwise solidify) to form a solid or semisolid fixative, and are compatible with body fluids and/or pharmaceutically acceptable liquid vehicles (for example, physiological or 0.9% sodium chloride saline solution). Suitable fixatives include styrene, acrylonitrile, natural rubber, neoprene polyurethane, silicone rubber, and/or epoxy resin. The fixative should be selected to minimize impact on the optical fiber during the curing process. For example, outgassing during curing can result in the formation of deposits on the optical surfaces of the optical fiber that can require extensive post-production processing to remove. In a preferred embodiment the fixative is an epoxy resin, for example the product currently known as ANGSTROM BOND® 9112. It should be appreciated that when an optical fiber with a jacket 120 is utilized the fixative contacts the jacket 120, whereas if an optical fiber without a jacket is utilized the fixative contacts the cladding 110.

In some embodiments of the inventive concept, the fixative can be selected to be transparent or at least partially transmissive to light. In such embodiments, the amount and/or distribution of fixative can be characterized by monitoring light transmitted through the fixative of the sheathed optical fiber (for example, by illuminating an end of the sheathed optical fiber and characterizing light emitted from the fixative-occupied gap 130).

FIG. 2 shows a longitudinal section of a terminus of an optical device of the inventive concept. As in FIG. 1B, the device includes a core 200, a cladding 210, a jacket 220, and a sheath 240. In this instance the gap or intraluminal space 230 between the inner wall of the sheath 240 and the surface of the jacket 220 is occupied by a fixative. The terminus of the optical appliance includes a face 250. The face 250 can be configured to optimize optical coupling with a source of electromagnetic energy. In prior art devices such optical coupling is often provided using active optics, for example a lens, that focus or otherwise direct light into the core of an optical fiber. Such active optics, however, add weight and bulk that is highly undesirable in an optical device configured for insertion into the peripheral vasculature. Towards this end, a face 250 of the optical device can be configured to provide an essentially planar presentation, wherein the plane of the face 250 is within 3° of normal to the major axis of the sheath 240. In a preferred embodiment the plane of the face 250 is within 1° of normal to the major axis of the sheath 240. This feature permits accurate, head-on alignment with a suitable source of electromagnetic energy when the optical device is utilized with a fitting that aligns with the major axis of the sheath 240.

The face 250 can also have a surface finish that reduces loss of light due to reflection and diffraction. For example, the face 250 can have a surface roughness of less than 50 μm, less than 25 μm, less than 5 μm, less than 3 μm, or less than 1 μm. In a preferred embodiment of the inventive concept, the face 250 has a surface roughness of less than 3 μm. Surface roughness can also be expressed in terms of a scratch and dig surface defect standard. Using such a standard, the face 250 can have a scratch/dig rating of 40/20 or less. In a preferred embodiment of the inventive concept the surface roughness of the face 250 is about 10/5 or better when compared against a scratch and dig surface defect standard.

It is contemplated that in use, an optical device of the inventive concept can be utilized by inserting it within an intravenous catheter or cannula. In such an embodiment, the outer diameter of the sheath of the optical device can be selected to be less than that of an inner diameter of such an intravenous catheter or cannula. The resulting gap between the sheath and the inner wall of the cannula can, if desired, support the flow of a pharmacologically acceptable fluid (for example, 0.9% sterile saline) around and past the optical device when in use. Similarly, the length of the optical device can be selected such that a terminus remains within an intravenous catheter when in use. In some embodiments of the inventive concept, the length of the optical device is selected so that the optical device lies entirely inside of a catheter or cannula when in use, with a terminus of the optical device positioned between about 1 mm and about 8 mm from an opening of the catheter or cannula that is exposed to the interior of a vasculature. In other embodiments the length of the optical device is selected so that the optical device lies entirely inside of a catheter or cannula when in use, with a terminus of the optical device positioned between about 2 mm and about 6.5 mm from an opening of the catheter or cannula that is exposed to the interior of a vasculature. It is contemplated that an optical device of the inventive concept can be used in conjunction with a suitable positioning device that includes a fitting or similar device which permits coupling to an intravenous catheter or cannula, and that the length of the optical device can be selected to accommodate such a device and catheter or cannula. Suitable lengths for the optical device can range from about 38 mm to about 89 mm. In a preferred embodiment the length of the optical device is about 70 mm.

Another embodiment of the inventive concept is a method for producing an optical device suitable for illuminating the vasculature of a mammal. FIG. 3 schematically depicts such a method. Initially a sheath is secured 300, for example in a vertical orientation relative to a major axis of the sheath. A flowable fixative or fixative precursor (for example, a resin-based fixative prior to curing) is then introduced to the interior of the sheath 310. This can, for example, be accomplished by injecting the flowable fixative or fixative precursor into the opening at the upper terminus of the sheath. An optical fiber is then introduced into the interior of the sheath 320. This can displace excess flowable fixative or fixative precursor within the sheath; this excess fixative is subsequently removed 330. The fixative is then cured 340, for example by heating in an oven or similar device, affixing the optical fiber to the interior of the sheath. The ends of the sheath and the optical fiber are then processed 350, for example by polishing to produce the required surface finish and planar orientation of the face of the optical device relative to a major axis of the sheath. Optionally, the sheath can be trimmed to the desired length prior to processing to provide the desired orientation and surface roughness of a face of the optical device.

In an alternative embodiment of a method for producing an optical device of the inventive concept, the optical fiber is produced by an extrusion process that includes application of a fixative to the surface of the optical fiber. In such an extrusion process the optical fiber can be produced with or without a jacket. The extruded optical fiber with fixative applied to its surface can then be introduced into a sheath and the fixative cured, as described above. In some embodiments, a length of such extruded optical fiber is placed within a length of sheath material or tubing, where the length exceeds that of the optical device. The optical fiber and sheath combination can then be trimmed or cut to a length or lengths approximating that of the final optical device to provide one or more intermediate pieces. Such trimming or cutting can occur either before or after curing of the fixative. Following curing of the fixative, the intermediate pieces can then be finished by appropriate cutting, trimming, and/or polishing processes in order to provide one or more finished optical device(s).

It should be appreciated that, when intended for use in applications involving insertion into a catheter or cannula, the dimensions of the lumen of the cannula within which the optical device lies drive the selection of the sheath and hence the optical fiber components of the optical device. As noted above, in some applications it can be desirable to provide a flow of a pharmacologically acceptable fluid through a lumen of a catheter or cannula that is also occupied by an optical device of the inventive concept. The dimensions of such catheters and cannulas is dependent on their intended use and the dimensions of the vascular space into which they are inserted. For example, a catheter intended for pediatric use in a peripheral vein can be a 22 gauge catheter, wherein a catheter used in veterinary practice or in emergency situations can be as large as 18 gauge. Optical devices of the inventive concept for use in such catheters can be selected so as to permit sufficient residual volume between the sheath of the optical device and the inner wall of the lumen of the catheter or cannula to permit fluid flow. For example, the minimum flow rate through a 24 gauge catheter can be selected as a minimum desirable flow rate through a catheter or cannula with a lumen occupied by an optical device of the inventive concept. This flow rate can be used in combination with the size of the catheter or cannula to be used to determine the maximum acceptable diameter of the optical device (and hence the sheath), which in turn can be used to determine the maximum acceptable diameter of the optical fiber. Examples of such calculations performed for optical devices for use in 18, 20, and 22 gauge intravenous catheters are provided in FIG. 4.

As noted above, optical devices of the inventive concept are suitable for illumination of the vasculature of a vertebrate. In a method of the inventive concept, an optical device that includes a sheathed optical fiber wherein an optical fiber lies entirely within a sheath is introduced into the vasculature of a mammal (for example, a human). In such an embodiment a fixative occupies space between the optical fiber and the sheath. In a preferred embodiment the optical device is placed essentially centrally within a peripheral vein. Illumination is provided by introducing electromagnetic energy (for example, by providing optical communication with a source of electromagnetic energy) to the terminus of the optical device that lies outside of the vascular space, such that electromagnetic energy exits a terminus of the optical device that lies within the vascular space. In some embodiments of the inventive concept the optical device within the vascular space lies within an intravascular catheter or cannula, such that the optical device itself is not directly exposed to the intravascular space.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A sheathed optical fiber comprising: a pliant and resilient metal comprising a lumen, wherein the lumen has a first diameter; an optical fiber placed within the lumen in its entirety and having a length essentially identical to that of the pliant and resilient metal sheath, having second diameter and comprising an optical medium that is substantially transparent to at least one of the group of wavelengths of light consisting of ultraviolet, visible, and infrared light, wherein the second diameter is less than the first diameter, the space defined by the first diameter and the second diameter providing the boundaries of an intraluminal space; and a fixative, wherein the fixative occupies at least a portion of the intraluminal space, and wherein the pliant and resilient metal sheath is configured to maintain a straight or slightly curved configuration, wherein the optical fiber comprises a core, a cladding, and a jacket.

2. The sheathed optical fiber of claim 1, wherein the pliant and resilient metal sheath comprises a biocompatible material.

3. The sheathed optical fiber of claim 1, wherein the optical medium comprises silica.

4. The sheathed optical fiber of claim 1, wherein the fixative is substantially transparent to visible light.

5. The sheathed optical fiber of claim 1, wherein the fixative occupies at least 95% of the intraluminal space.

6. The sheathed optical fiber of claim 1, wherein the distribution of the fixative within the intraluminal space is configured to contain a fragment of a damaged optical fiber.

7. The sheathed optical fiber of claim 1, wherein the fixative is compatible with a pharmaceutically acceptable solution.

8. The sheathed optical fiber of claim 1, wherein the optical fiber further comprises a first terminus and a second terminus.

9. The sheathed optical fiber of claim 8, wherein the first terminus and the second terminus have a first face and a second face respectively, and wherein both the first face and the second face are within 0° to 3° of perpendicular to a major axis of the sheathed optical fiber.

10. The sheathed optical fiber of claim 8, wherein the first face and the second face each have a surface roughness of less than or equal to 0.3 microns.

11. The sheathed optical fiber of claim 1, wherein the fixative comprises an epoxy resin.

12. The sheathed optical fiber of claim 1 wherein the pliant and resilient metal sheath comprises passivated stainless steel.

13. The sheathed optical fiber of claim 1, wherein outer diameter of the pliant and resilient metal sheath is dimensioned to lie within a lumen of an intravenous catheter such that an average distance of at least 0.04 mm lies between the surface of the sheath and the wall of the lumen.

14. The sheathed optical fiber of claim 1, wherein the outer diameter of the pliant and resilient metal sheath is less than 0.75 mm.

* * * * *